(12) United States Patent
Bougaret et al.

(10) Patent No.: US 9,061,015 B2
(45) Date of Patent: Jun. 23, 2015

(54) STABLE SOLID DISPERSION OF A DERIVATIVE OF VINCA ALKALOID AND PROCESS FOR MANUFACTURING IT

(75) Inventors: Joel Bougaret, Francarville (FR); Elie Leverd, Castres (FR); Marie-Dominique Ibarra, Souilhanels (FR)

(73) Assignee: PIERRE FABRE MEDICAMENT, Boulogne-Billancourt (FR)

( * ) Notice: Subject to any disclaimer, the term of this patent is extended or adjusted under 35 U.S.C. 154(b) by 565 days.

(21) Appl. No.: 11/667,998

(22) PCT Filed: Dec. 20, 2005

(86) PCT No.: PCT/EP2005/056965
§ 371 (c)(1),
(2), (4) Date: May 17, 2007

(87) PCT Pub. No.: WO2006/069938
PCT Pub. Date: Jul. 6, 2006

(65) Prior Publication Data
US 2008/0089935 A1   Apr. 17, 2008

Related U.S. Application Data

(66) Substitute for application No. PCT/EP2005/056965, which is a continuation of application No. 11/025,348, filed on Dec. 30, 2004.

(30) Foreign Application Priority Data

Dec. 30, 2004   (FR) ..................................... 04 14069

(51) Int. Cl.
| | | |
|---|---|---|
| *A61K 31/55* | (2006.01) | |
| *A61K 47/30* | (2006.01) | |
| *A61K 31/4375* | (2006.01) | |
| *A61K 9/48* | (2006.01) | |
| *A61K 9/20* | (2006.01) | |
| *A61K 9/28* | (2006.01) | |

(52) U.S. Cl.
CPC .......... *A61K 31/4375* (2013.01); *A61K 9/2018* (2013.01); *A61K 9/2846* (2013.01); *A61K 9/2866* (2013.01); *A61K 9/2886* (2013.01); *A61K 9/4808* (2013.01)

(58) Field of Classification Search
None
See application file for complete search history.

(56) References Cited

U.S. PATENT DOCUMENTS

| | | |
|---|---|---|
| 2001/0048946 A1 | 12/2001 | Ghebre-Sellassie |
| 2002/0004070 A1* | 1/2002 | Rudnic et al. ................. 424/468 |
| 2003/0109639 A1* | 6/2003 | Lippold et al. ................ 525/205 |
| 2003/0212102 A1 | 11/2003 | Koretke et al. |
| 2005/0048119 A1* | 3/2005 | Nangia et al. ................. 424/473 |

FOREIGN PATENT DOCUMENTS

| | | | |
|---|---|---|---|
| WO | WO-00/05939 A2 | | 2/2000 |
| WO | WO-01/95939 A1 | | 12/2001 |
| WO | WO 03/101383 | * | 12/2003 |
| WO | WO-03/101383 A2 | | 12/2003 |

OTHER PUBLICATIONS

Voss et al, 2009. Synthesis and SAR of vinca alkaloid analogues. Bioorganic and Medicinal Chemistry Letters, vol. 19:1245-1249.*
Johnson, 2005. Vinorelbine: An update and review of activity. Clinical oncology, vol. 8:353-357.*
Fahy et al, 2002. New method of synthesis of vinca alkaloid derivatives. Bioorganic and Medicinal Chemistry Letters, vol. 12:505-507.*
Moldvai et al, 1997. Sulfonamide derivatives of some vinca alkaloids with cardiovascular activity. Part 84. Synthesis of Vinca alkaloids and related compounds. Archiv de Pharmaczie, vol. 33(6):190-198.*
Leuner and Dressman, 2000. Improving drug solubility for oral delivery using solid dispersions. European Journal of Pharmaceutics and Biopharmaceutics, vol. 50:47-60. (provided by applicant in the May 17, 2007 IDS and Jul. 24, 2007 IDS).*
Wagner et al, 2000. development of disintegrating multiple-unit tablets on a high-speed rotary tablet press. European journal of Pharmaceutics and Biopharmaceutics, vol. 50:285-291.*
The online Encarta® World English Dictionary, North American Edition, accessed Jan. 30, 2011, definition of dispersion.*
The online Encarta® World English Dictionary, North American Edition, accessed Jan. 30, 2011, definition of colloids.*
Marty (Annals of Oncology, 12, 1643-1649, 2001) Oral vinorelbine pharmacokinetics and absolute bioavailability.*
Leuner et al., "Improving drug solubility for oral delivery using solid dispersions," European Journal of Pharmaceutics and Biopharmaceutics, Elsevier Science Publishers B.V., vol. 50, No. 1, Jul. 2000, pp. 47-60.
New Dosage form and new techniques of drugs, Apr. 1998, 1st Edition.

* cited by examiner

*Primary Examiner* — Tigabu Kassa
(74) *Attorney, Agent, or Firm* — Birch, Stewart, Kolasch & Birch, LLP

(57) ABSTRACT

This invention relates to solid and stable dispersions of a hydrosoluble derivative of vinca alkaloids in at least one polyethyleneglycol with a molecular mass between 800 and 30 000.

13 Claims, 1 Drawing Sheet

STABLE SOLID DISPERSION OF A DERIVATIVE OF VINCA ALKALOID AND PROCESS FOR MANUFACTURING IT

This application is the National Phase of PCT/EP2005/056965 filed on Dec. 20, 2005, which is a continuation of U.S. application Ser. No. 11/025,348 filed on Dec. 30, 2004 and which claims priority under 35 U.S.C. 119(a) to Patent Application No. 0414069 filed in France on Dec. 30, 2004. Both of these prior applications are hereby expressly incorporated by reference into the present application.

FIELD OF THE INVENTION

This invention relates to solid and stable dispersions of hydrosoluble derivatives of *vinca* alkaloids and more particularly derivatives of vinorelbine, particularly vinorelbine ditartrate in at least one polyethyleneglycol, which are intended to be incorporated into pharmaceutical compositions for oral administration of such a *vinca* derivative.

BACKGROUND OF THE INVENTION

Antineoplastic chemotherapy was initially developed using intravenous methods. The arguments in favor of this administration method are:
- lesser gastrointestinal toxicity,
- total bioavailability, and
- potentially lower inter and intra patient exposure variations than with an oral method.

However, the intravenous method is associated with serious disadvantages that limit its use: the morbidity of vein access, possible complications of central vein channels (infection, thrombosis), the risk of extravasation.

For several years, oral forms of antineoplastic chemotherapy have developed increasingly due to the real benefit possible for the patient. Furthermore, pharmaco-economic considerations that are becoming increasingly important in the choice of therapeutic strategies, are also leading towards the development of oral treatments.

A lot of exploratory work has been carried out on the possible use of molecules intended for the treatment of cancer and administrated by mouth, for former active principles (for example etoposide, cyclophosphamide and idarubicine), new synthetic derivatives of fluoropyridines (for example UFT, capecitabine, S-1), derivatives of platinum (for example JM-216) or Vinca alkaloids (e.g. vinorelbine).

Therefore this invention also concerns stable pharmaceutical compositions for oral administration of vinca alkaloids, and particularly vinorelbine in dispersed form.

Vinorelbine or 3'4'-Didehydro-4'-desoxy-8'-norvincaleucoblastine is an alkaloid derivative of vinca which exerts a cytostatic effect by inhibition of the polymerization of tubulin.

Vinorelbine, and more particularly a salt of vinorelbine, vinorelbine ditartrate, is also active in the treatment of large cell lung cancer and breast cancer. An injectable form was marketed for the first time in France in 1989. It is now marketed throughout the world in the form of a solution to be diluted for perfusion, to a concentration of 10 mg/ml expressed in basic vinorelbine and distributed in flasks with unit volumes of 1 and 5 ml.

More recently, an oral formulation of vinorelbine in solution was developed and put on the market under the name of NAVELBINE Oral® soft capsules. It is in the form of a soft gelatin capsule containing vinorelbine ditartrate and an excipient mix comprising polyethyleneglycol, glycerol, ethanol and water. The average molecular mass of polyethyleneglycol is between 200 and 600: these are liquid polyethyleneglycols such as MACROGOL 400. Unit doses expressed in basic vinorelbine are between 5 mg and 100 mg, and more advantageously equal to 20 mg, 30 mg, 40 mg and 80 mg.

These soft capsules were described in a patent application R. P. Scherer Technologies, Inc. WO 03/101383.

SUMMARY OF THE INVENTION

Pharmaceutical compositions according to this invention are intended for oral administration of alkaloid derivatives of *vinca* and particularly vinorelbine, in dispersed form. They contain the hydrosoluble derivative of *vinca* alkaloid, advantageously a salt of vinorelbine, and more particularly ditartrate dispersed in semi-solid or solid polyethyleneglycols.

DETAILED DESCRIPTION OF THE INVENTION

Figure 1A:
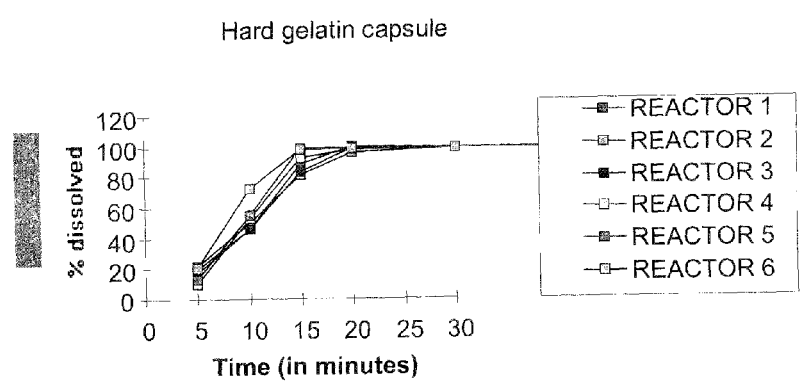
FIG. 1A is a graph showing the percentage of vinorelbine ditartrate in a hard gelatin capsule that was dissolved in a reactor with 900 ml water at 37° C. and 50 rpm vs. time in minutes. The dissolution rate was tested for 6 samples of hard gelatin capsules in reactors 1-6, respectively. The process used was the rotating plate process given in the European Pharmacopoeia 2.9.3.

More precisely, the stable solid dispersion according to the invention is associated with a hydrosoluble derivative of vinca alkaloid, particularly in at least one polyethyleneglycol with a molecular mass between 800 and 30,000, and more particularly a polyethyleneglycol with a molecular mass of between 1,000 and 6,000.

Polyethyleneglycols chosen in the invention have an average molecular mass greater than about 800. When the molecular mass is between 800 and 2,000, they are in semi-solid form, and when the molecular mass is higher, they are in solid form. They are differentiated from each other by their melting point, as indicated in the table below.

|  | Polyethyleneglycol (average molecular mass) | | | | | | |
| --- | --- | --- | --- | --- | --- | --- | --- |
|  | 1000 | 1500 | 4000 | 6000 | 8000 | 20000 | 30000 |
| Melting point | 37° C. to 40° C. | 44° C. to 48° C. | 50° C. to 58° C. | 55° C. to 63° C. | 60° C. to 63° C. | 60° C. to 63° C. | 65° C. to 70° C. |

According to one advantageous embodiment of this invention, the ratio of the masses of the hydrosoluble derivative of vinca alkaloids and more particularly firstly vinorelbine ditartrate, and secondly polyethyleneglycol, is between 1.5:1 and 1:10 and preferably between 1:3 and 1:6.

These dispersions of the derivative of vinca alkaloids or the salt of vinorelbine in polyethyleneglycols according to this invention form a solid dispersion. In general, the use of the solid dispersions technology in the pharmaceutical formulation domain is known. The first reason for the development of solid dispersions is based on the possibility of improving dissolution and therefore potentially the bioavailability of active principles that are not very soluble in water and are administered by mouth.

The use of hydrophilic polymers such as polyethyleneglycols, polyvinylpyrrolidone or cellulose derivatives tends towards this hydrosolubilisation. Within the context of this invention, solid dispersions are not used with the intention of increasing the dissolution rate of active constituents. Hydrosoluble derivatives of vinca alkaloids and particularly vinorelbine salts, and more particularly ditartrate, are very soluble in water and their wettability characteristics do not cause any problem.

However, unexpectedly, galenic forms of hydrosoluble derivatives of vinca alkaloids and particularly vinorelbine salts according to this invention are more stable.

Thus, vinorelbine ditartrate must be kept at a temperature of below −15° C., regardless of its form (amorphous or crystalline) and its degree of division (unground, ground or micronized).

On the other hand, solutions of vinorelbine ditartrate can be kept at temperatures between +5° C. and +3° C. This is the case both for the injectable water based solution for injectable preparations, and for the soft capsules filling solution composed of liquid polyethyleneglycol, glycerol, ethanol and water. Therefore, it appeared that the solubilization operation was responsible for better stability.

Surprisingly, in the pharmaceutical compositions according to this invention, hydrosoluble derivatives of vinca alkaloids and particularly vinorelbine ditartrate which is in the dispersed powder state, are at least as stable, or even more stable, than the soft capsules in which they are dissolved.

A preparation of dispersions of hydrosoluble derivatives of vinca alkaloid, and particularly vinorelbine, and more particularly vinorelbine ditartrate, always begins with a mix of this active principle with polyethyleneglycol in the molten state. To achieve this, the said polyethyleneglycol will be previously heated to a temperature slightly greater than its melting temperature to bring it into the liquid state so that it can be mixed with the hydrosoluble derivative of vinca alkaloid while stirring. The process terminates with a cooling operation of the said dispersion to bring it into the solid state. If a polyethyleneglycol with a high molar mass is used, it will preferably be heated in the presence of a plastifier, which will bring the said solid polyethylene into the liquid state without exceeding a temperature of the order of 80° C.

The first step in the preparation of the solid dispersion can advantageously be done as follows:
either discontinuously: manufacturing in tank, before distribution of the mix for example in hard gelatin capsules or by the use of techniques such as molding injection, or continuously using hot extrusion techniques.
These techniques have two advantages:
the concentration of the active principle in the final mix can be as high as 60%, which for example allows large unit doses,
the residence time of the active principle in the extruder, for which the duration of its exposure to high temperatures is short so that a vinorelbine salt can be used although it is sensitive to heat with polyethyleneglycols with a high molecular mass.

The dispersions obtained may be in divided form, for example in the form of pellets, or in monolithic form, for example in the form of tablets. In order to protect manufacturing personnel or the patient from risks of exposure to cytotoxic vinorelbine salts, the final pharmaceutical forms will be distributed in hard gelatin capsules or they will be coated tablets.

After mixing and cooling, polyethyleneglycol and vinorelbine give a mass that can be treated differently as a function of the particular form searched for. It may be directly poured into the hard gelatin capsules to lead to a monolithic form after the said hard gelatin capsules have been cooled.

Traditionally, the hard gelatin capsules are composed of gelatin, hydroxypropylmethycellulose or extracellular bacterial polysaccharide obtained using Aureobasidium pullulans, known under the name of pullulan.

According to one variant of the process according to this invention, the stable solid dispersion is extruded to obtain pellets to be used to make hard gelatin capsules or tablets. In the latter case, coating is done during the actual manufacturing operation, for example using a co-extruded technique, the dispersion being effectively co-extruded with a natural or synthetic film-forming polymer to obtain film-coated tablets directly.

As a variant, this type of coating operation may also be done during a later additional manufacturing step, for example requiring fluidized air bed or turbine coating techniques.

In both coating variants, the coating may advantageously be obtained using a film forming polymer, with natural or synthetic origin, and particularly cellulose derivatives such as hydroxypropylmethylcellulose, hydroxypropylcellulose or acrylic ester or modified methacrylic ester copolymers or polyethyleneglycols with high molecular weight.

When the said stable solid dispersion uses polyethyleneglycols with low molecular mass (800-2,000), technical additives such as structuring agents, and particularly silica, polyethylene oxide, microcrystalline cellulose, can be added. The proportions in which these additional structuring agents will be present vary between 0.05% and 10%, and preferably between 0.5% and 5%.

Finally, it should be noted that when polyethyleneglycols with a high molecular mass are used, it may be advantageous to add plastifiers to avoid an excessive increase in the melting temperature so that they can be obtained in the liquid state in the context of the first mixing operation with vinca derivatives. Examples of plastifiers include ester citrates, triacetine, etc.

The following examples describe some possible formulations and preparation processes:

Example 1

The use of a semi-solid polyethyleneglycol involves the incorporation of a structuring agent such as silica, as described in the following composition:

| | |
|---|---|
| Vinorelbine ditartrate (in amorphous form) | 55.40 mg |
| i.e. vinorelbine | 40.00 mg |
| Silica | 3.00 mg |
| Polyethyleneglycol 1000 | qsq 330.00 mg |

The preparation is made discontinuously using a preliminary hot mix in a tank before distribution in gelatin capsules.

Example 2

The use of a solid polyethyleneglycol with a high melting point imposes the use of a plastifier and the use of a hot extrusion manufacturing process.

The following hot mix was prepared continuously in a co-extruder with a double screw:

| | |
|---|---:|
| Vinorelbine ditartrate (in amorphous form) | 55.40 mg |
| i.e. vinorelbine | 40.00 mg |
| Triethyl citrate | 6.00 mg |
| Polyethyleneglycol 6000 | qsq 150.00 mg |

Example 3 below gives a complete illustration of this invention and describes a process of production. It relates to a gelatin capsule containing 40 mg of vinorelbine dispersed in polyethyleneglycol 1500.

Example 3

The exact composition of the contents is:

| | |
|---|---:|
| Vinorelbine ditartrate (in amorphous form) | 55.40 mg |
| i.e. vinorelbine | 40.00 mg |
| Polyethyleneglycol 1500 | qsq 330.00 mg |
| Size 2 gelatin capsule | 1 |

The manufacturing process includes the following steps:
polyethyleneglycol 1500 is heated to a temperature of between 55° C. and 60° C.,
dispersion under mechanical stirring of vinorelbine ditartrate,
filling in size 2 hard gelatin capsules, with 330 mg of mix per hard gelatin capsule,
cooling to ambient temperature.

The essential constituent of the gelatin capsule casing is a hydrophilic polymer which, as mentioned above, may be gelatin or hydroxypropylmethylcellulose (HPMC) or pullulan.

There is no need to seal the gelatin capsules since no leakage occurs during storage. However, with regard to the cytotoxicity of the vinorelbine, it is recommended that it should be sealed for safety reasons. This is done either by stretch wrapping, or by spraying with a hydro-alcohol spray.

This composition has an excellent physicochemical stability: degradation of the dispersed vinorelbine formulated in hard gelatin capsules after 6 months of storage at 25° C./60% RH (severe temperature condition) is:
very significantly less than the degradation observed for vinorelbine alone,
less than or equal to the degradation observed in soft capsules.

The results are expressed below:

| | | Formulated vinorelbine | | |
|---|---|---|---|---|
| | Vinorelbine ditartrate | Hard gelatin capsule | HPMC capsule | Soft capsule |
| Physical state of vinorelbine ditartrate | Powder | Dispersed powder | Dispersed powder | Solution |
| Total impurities Including identified impurities: | +1.87 | +0.70 | +0.62 | +0.76 |
| S/D6 | +1.02 | — | — | — |
| 6'-N-oxyvinorelbine | +0.37 | — | — | — |
| 6'-N-methylvinorelbine | +0.05 | +0.10 | +0.10 | +0.15 |
| 4-0-deacetylvinorelbine | +0.05 | +0.04 | +0.08 | +0.37 |
| 23-0-demethyl-vinorelbine | — | +0.15 | +0.17 | +0.16 |

Variation of the content of impurities (in % relative) after 6 months 25° C./60% RH compared with t0.

Other hydrophilic polymers such as polyethyleneglycols were tested. The stability of vinorelbine in the presence of these other polymers is significantly lower: after only 1 month at 25° C./60% RH, the variation of the content of impurities compared with t0 was +7.63% and +29.08% for polyvinylpyrrolidone and a cellulosic ether respectively.

Figure 1B:
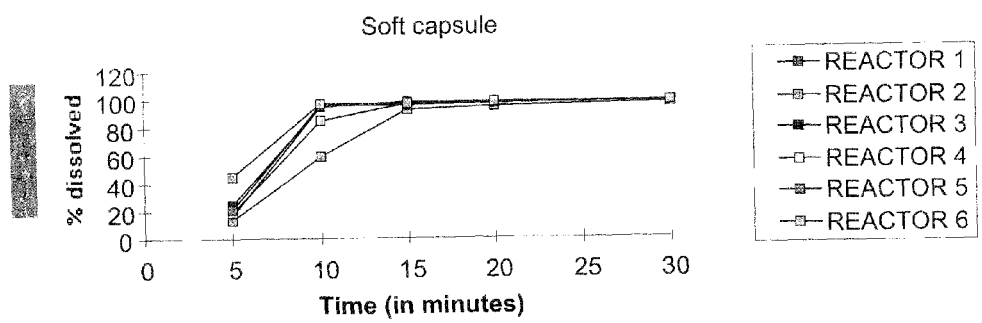
FIG. 1B is a graph showing the percentage of vinorelbine ditartrate in a soft capsule that was dissolved in a reactor with 900 ml water at 37° C. and 50 rpm vs. time in minutes. The dissolution rate was tested for 6 samples of soft capsules in reactors 1-6, respectively. The process used was the rotating plate process given in the European Pharmacopoeia 2.9.3.

Furthermore, and unexpectedly, the dissolution rate of vinorelbine ditartrate contained in the hard gelatin capsule in example 3 above, in the dispersed state, is very similar to the dissolution dynamics of vinorelbine ditartrate contained in the dissolved state in the soft capsule. The dissolution profiles in 900 ml of water at 37° C., 50 rpm, for six samples of a batch of each galenic form, are given in FIGS. 1A and 1B appended. The process used is the rotating plate process given in the European Pharmacopoeia 2.9.3. Dissolution of vinorelbine ditartrate is 100° complete in less than 30 minutes.

Unit doses of hard gelatin capsules, expressed in basic vinorelbine, are between 5 and 100 mg and are advantageously equal to 20 mg, 30 mg, 40 mg and 80 mg.

However, this invention can be used particularly to obtain unit doses of more than 100 mg, and up to 300 mg, by injection molding.

The invention claimed is:

1. A storage-stable pharmaceutical composition configured for oral administration, said composition consisting of a solid dispersion consisting of (a) a hydrosoluble salt of vinorelbine which is in a dispersed powder state, (b) at least one solid or semi-solid polyethyleneglycol having a molecular mass of between 800 and 30,000 and, optionally, (c) one or more of (i) a plastifier, (ii) a structuring agent, and (iii) a compression excipient,
wherein the ratio of the masses of the hydrosoluble salt of vinorelbine to the polyethyleneglycol is between 1:3 and 1:6,
wherein the increase in the amount of impurities present in the pharmaceutical composition is not greater than the increase in the amount of impurities present in the powdered hydrosoluble salt of vinorelbine after the pharmaceutical composition and the powdered hydrosoluble salt of vinorelbine have each been stored at 25° C. and 60% relative humidity for 6 months.

2. The pharmaceutical composition according to claim 1, wherein the salt of vinorelbine is vinorelbine ditartrate.

3. The pharmaceutical composition according to claim 1, wherein the polyethyleneglycol has a molecular mass of between 1,000 and 6,000.

4. The pharmaceutical composition according to claim 1, wherein the dispersion has at least one of a plastifier and a structuring agent.

5. The pharmaceutical composition according to claim 1, wherein the dispersion is in monolithic form.

6. The pharmaceutical composition according to claim 5, wherein the dispersion is placed in a hard gelatin capsule.

7. The pharmaceutical composition according to claim 5, wherein the dispersion is in the form of a tablet, wherein the tablet has a compression excipient.

8. The pharmaceutical composition according to claim 1, wherein the dispersion is in the form of divided pellets.

9. The pharmaceutical composition according to claim 8, wherein the divided pellets are distributed in a hard gelatin capsule.

10. The pharmaceutical composition according to claim 2, wherein the polyethyleneglycol has a molecular mass of between 1,000 and 6,000.

11. The pharmaceutical composition according to claim 2, wherein the dispersion has at least one of a plastifier and a structuring agent.

12. The pharmaceutical composition according to claim 3, wherein the dispersion has at least one of a plastifier and a structuring agent.

13. A storage-stable pharmaceutical composition configured for oral administration, said composition consisting of a solid dispersion consisting of (a) a hydrosoluble salt of vinorelbine which is in a dispersed powder state, (b) at least one solid or semi-solid polyethyleneglycol having a molecular mass of between 800 and 30,000 and, optionally, (c) one or more of (i) an ester citrate or triacetine plastifier, (ii) a silica, polyethylene oxide, or microcrystalline cellulose structuring agent, and (iii) a compression excipient,
  wherein the ratio of the masses of the hydrosoluble salt of vinorelbine to the polyethyleneglycol is between 1:3 and 1:6,
  wherein the increase in the amount of impurities present in the pharmaceutical composition is not greater than the increase in the amount of impurities present in the powdered hydrosoluble salt of vinorelbine after the pharmaceutical composition and the powdered hydrosoluble salt of vinorelbine have each been stored at 25° C. and 60% relative humidity for 6 months.

* * * * *